United States Patent [19]

Peppers

[11] Patent Number: 4,830,856
[45] Date of Patent: May 16, 1989

[54] CHELATION PRODUCT

[76] Inventor: James M. Peppers, P.O. Box 200038, Arlington, Tex. 76006-0038

[21] Appl. No.: 7,173

[22] Filed: Jan. 27, 1987

[51] Int. Cl.$^4$ .................. A61F 13/02; A61L 15/06
[52] U.S. Cl. .................................. 424/449; 424/448; 424/DIG. 6
[58] Field of Search ................................ 424/449, 448

[56] References Cited

U.S. PATENT DOCUMENTS

| | | | |
|---|---|---|---|
| 2,698,823 | 1/1955 | Bersworth | 514/566 |
| 3,742,951 | 7/1973 | Zaffaroni | 424/434 |
| 4,201,211 | 5/1980 | Chandrasekaran et al. | 424/449 |
| 4,486,193 | 12/1984 | Shaw et al. | 424/449 |

FOREIGN PATENT DOCUMENTS 139127A 2/1985 European Pat. Off. ............ 424/449

*Primary Examiner*—Thurman K. Page
*Assistant Examiner*—P. L. Prater
*Attorney, Agent, or Firm*—James E. Bradley

[57] ABSTRACT

A medical bandage product and method for continually administering a chelating agent through the skin of a living body in a controlled manner. The product includes a membrane of selected area adapted for placement against the skin, the membrane being formed of an aqueous solution release rate controlling material. An aqueous liquid impermeable member is connected about the edges of the membrane and having sides forming a reservoir. The aqueous solution consists essentially of a chelation agent in selected proportion, a transportation agent in selected proportion to the chelation agent, a pH adjustment agent in selected amount, and a vasodilator in selected proportion to the chelation agent and the balance water. Means for retaining the product against the skin is provided. Also discloses the method for transporting a chelating agent throughout body tissues with use of the product.

16 Claims, 1 Drawing Sheet

CHELATION PRODUCT

FIELD OF THE INVENTION

This invention generally relates to chelation therapy treatment and more particularly pertains to a method and product for transporting a chelating agent through the skin and subsequently throughout the vascular systems and tissues of living subjects.

BACKGROUND OF THE INVENTION

The need fulfilled by chelation therapy treatment is to remove toxic or undesirable metals such as lead, mercury, cadmium, calcium, and the like from living bodies. For example, excessive concentrations of lead are accumulated in a subject's body through ingestion of contaminated water from lead plumbing, fish from contaminated water, lead in paints, pesticides, lead used in manufacturing processes, and by inhalation of air contaminated by auto emissions, lead smelting and the like. Mercury accumulates from sources similar to lead. Mercury also leaches out of amalgam fillings used in dental work. Calcium is a building block of the cholesterol/triglycerides plaque which builds up in human vascular systems. This plaque consequently leads to coronary problems, blood circulation problems, strokes, and the like.

The preferred modality which has developed to remove these metals has been chelation therapy treatments, administered intervenously.

Intervenous (I.V.) treatments are very effective, but have proven to be inconvenient, time consuming, and expensive. I.V. treatments further require skilled personnel and a suitable environment such as a clinic to be administered. All subjects, both human and animal, are reluctant to receive I.V. treatments on a continuing basis. The typical I.V. chelation therapy treatment takes a minimum of about three hours per treatment and the treatments may be administered at intervals of one to six times a week to a total of thirty to ninety treatments, or more, for example. The blind testing required by government agencies and some professional groups for I.V. chelation treatment has proven to be very difficult and almost impossible to conduct to complete satisfaction.

As an advantage over I.V. Chelation treatments, the present invention allows the subject to walk about conveniently, or otherwise exercise as appropriate, to establish good blood circulation during treatment. Subjects characterized by poor or impaired blood circulation are often candidates for chelation treatment. The chelation agent is excreted through the kidneys rather quickly and improved blood circulation tends to better distribute the chelation agent while it remains available in the system. The better distribution of course better utilizes such dosage of the chelation agent.

The EDTA series of polyaminocarboxylic acids has proven to be the most effective therapeutic chelating agents. Of these, the preferred agents are ethylene diamine tetra acetic acid (EDTA), and trans 1,2-cyclohexane diamine tetra acetic acid (CDTA), which are considered the best. EDTA is the agent most commonly used in medicine although CDTA has physical characteristics which makes it the superior to EDTA under certain circumstances and is the only compound found to be superior to EDTA as an overall complexing agent. EDTA is usually compounded as the disodium or tetrasodium salt and sometimes the calcium salt. Some of the commercial EDTA products are Cheladrate (Farmex), Disotate (Fellows), and Edetate (Abbott) and are those commonly used in chelation therapy. The sodium salt of EDTA is generally used in medicine because it increases the solubility of the chelating agents.

Informative sources concerning EDTA, as found in the development of the present invention, are U.S. Pat. Nos. 2,387,735; 2,407,645; 2,698,823; 2,781,291; 2,785,174; 3,308,065; 3,367,834; and 3,438,811. An informative publication is B. W. Halstead, *The Scientific Basis of EDTA Chelation Therapy*, Golden Quill Publishers, Inc., Colton, Calif., Copyright 1979. U.S. Pat. No. 2,698,823 discloses the uses of an ointment containing EDTA to give a creamy emulsion for daily skin application.

Dimethylsulfoxide (DMSO) is another significant component of the present invention. See U.S. Pat. Nos. 2,581,050 and 3,045,051. DMSO has been found to be an excellent solvent and penetrant through organic material with interactions between DMSO and other substances increasing in proportion to the polarizibility of the substance. DMSO is reported to be an unexcelled internal penetrating carrier of pharmaceuticals to any part of the body for a therapeutic effect. DMSO passes through cellular membranes and tissues. DMSO is able to penetrate endothelial coatings of the arterial walls, meninges of the brain, healthy skin, mucus membranes, and the various other tissues constituting a living body.

In the United States DMSO is currently regarded as an experimental drug for human use and has been released as a veterinary prescription drug. Currently, DMSO has been approved by the United States Food and Drug Administration (FDA), for use in treatment of interstitial cystitis. Other countries have used the drug therapeutically for more than two decades. The only mention of DMSO found in the therapeutic patent literature is in U.S. Pat. No. 4,201,211 where clonidine is administered transdermally by a skin patch product. There, the inventor recommends that the skin be prepared prior to the application of the skin patch by a skin permeation enhancing agent such as dodecylpyrrolidone, dimethyl lauramide or dimethylsulfoxide which is removed before application of the patch.

An informative publication is Morton Walker, *DMSO, The New Healing Power*, Devin-Adair Publishers, Old Greenwich, Conn., Copyright 1983. While this publication outlines many therapeutic qualities and characteristics of DMSO, it is to be noted that its primary function in the present invention is its excellent drug transporting characteristics.

Skin patch products, as used in the present invention, are generally available commercially for the transdermal administration of drugs such as nitroglycerin and the antihypertension drugs, clonidine, and captopril, for example. Such products are disclosed in more detail in U.S. Pat. Nos. 3,454,701; 4,201,211; 4,486,193; and 4,592,753.

An exemplary example of EDTA suitable for use in the present invention is Edetate Disodium U.S.P. Product No. 0277-20 as manufactured by Carter-Global Laboratories, Inc., Glendale, Ariz., 85301. The DMSO, used in the present invention, must be of pharmaceutical grade. The other compositions as may be used must also be of pharmaceutical grade.

It is to be noted that U.S. Pat. Nos. 2,698,823; 4,486,193; and 4,201,211 are hereby specifically incorporated into this specification by reference.

OBJECTS OF THE INVENTION

It is a primary object of the invention to provide a method and product for chelation therapy available to the patients of every licensed physician and veterinarian without the special clinics, personnel and time scheduling needed for I.V. chelation therapy.

An important object of the present invention is to provide a chelation method and product whereby the chelation treatment may be administered with good blood circulation and consequent improved distribution of the chelation agent throughout the subject during the treatment.

It is another important object of the present invention to provide a chelation method and product which may be administered to a subject by a layman upon direction and prescription of a licensed physician or veterinarian wherein the chelation treatment may be administered during the ordinary course of the daily activities of the subject without special facilities and personnel being required to administer the chelation treatment.

It is another object of the present invention to provide a chelation method and product which will reduce the cost of the chelation treatment to a small percentage of the present cost of I.V. chelation treatments.

It is another object of the invention to provide a chelation method and product wherein the chelation agent is administered into the subject in precise amount over an extended period of time wherein the possibility of postural hypotension, adversemyocardial contractility, and other adverse affects from rapid administration of chelation agents is substantially reduced.

It is another object of the invention to provide a method and product which may be more conveniently and positively tested for approval by government and professional organizations.

SUMMARY OF THE INVENTION

The foregoing and other objects and advantages of the invention are attained in a method for transporting a chelating agent throughout the body tissues of a living body, including the steps of placing on the bare skin of the body a medical bandage which has a reservoir containing an aqueous solution with a permeable membrane forming one side of the reservoir having a face in contact with the skin and its other face in contact with the aqueous solution, and an aqueous liquid impermeable member forming the remaining sides of the reservoir and connected about the edges of the membrane in a fluid type arrangement. The membrane is formed of an aqueous solution release rate controlling material that releases the aqueous solution from the reservoir at a continuous and controlled rate over time. Exemplary constituents of the aqueous solution are ethylene diamine tetracetic acid (EDTA), as the chelation agent, dimethyl sulfoxide (DMSO), as the transporting agent, in an amount selected in proportion to the EDTA, a pH adjustment agent an amount necessary to adjust the pH of said solution to a selected pH range, an optional vasodilator agent, and water. The porous membrane is attached and retained to the skin wherein the aqueous solution is transdermally transported into and throughout tissues of the living body. The essential therapeutic constituent of the aqueous solution is the chelation agent. The EDTA chelation agent is provided in selected proportion of the aqueous solution. The DMSO transporting agent is provided in selected proportion of the EDTA. The vasodilator agent is provided in selected proportion of the EDTA. The pH adjustment agent may be provided of an alkaline material such as sodium hydroxide. The pH adjustment agent also may be provided of an acid from the group of acetic acid, citric acid, ascorbic acid, and hydrochloric acid. The aqueous solution may be impregnated into a permeable member occupying the reservoir. Alternately, the aqueous fluid may be included within a gelling agent in the reservoir.

As part of the method, more than one of the medical bandages may be applied to the skin of the same body at the same time. Also, the method may include the placement of one after another of the medical bandages on the skin as the aqueous solution becomes depleted in a respective medical bandage.

The invention also includes a product for continually administering a chelating agent through the skin of a living body in a controlled manner with the product including a membrane of selected area adapted for placement against the skin with the membrane being formed of an aqueous solution release rate controlling material that releases an aqueous solution to the skin at a continuous rate over time. An aqueous liquid impermeable member is connected about the edges of the membrane and includes sides forming, together with the membrane, a reservoir containing the aqueous solution. For example, the aqueous solution contains the constituents of EDTA as the chelating agent in selected proportion to the aqueous solution, DMSO as the transporting agent, an optional vasodilator in proportion to the EDTA, in selected proportion to the EDTA, a pH adjustment agent an amount necessary to adjust the pH of the aqueous solution to a selected pH value, and with water as the remainder. The product is provided with an arrangement to attach and retain the medical bandage with the membrane disposed in contact with the skin of a subject.

DESCRIPTION OF A PREFERRED EMBODIMENT

Figure 1:
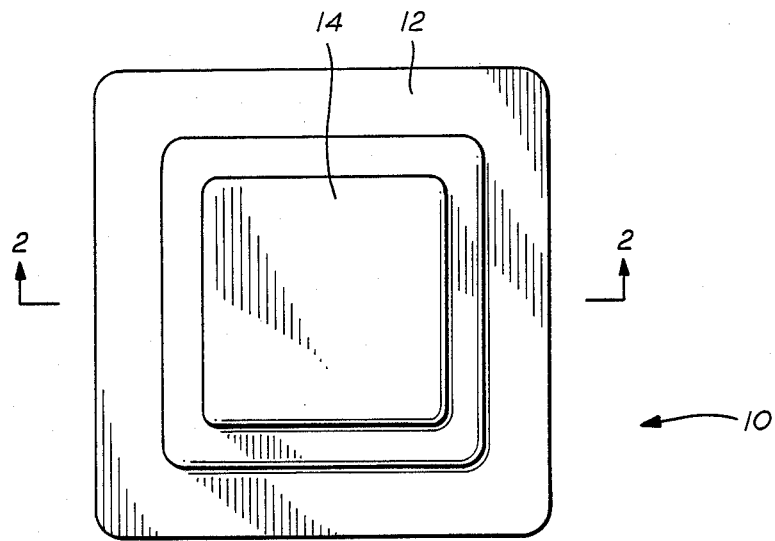
FIG. 1 is a side elevation view of the medical bandage product of the present invention.
Figure 2:
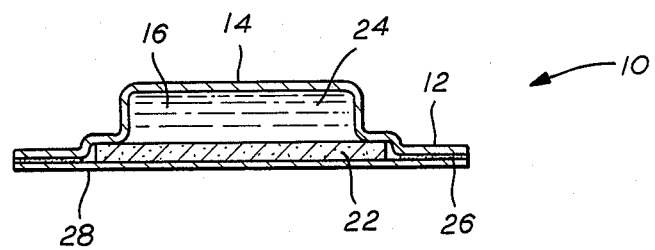
FIG. 2 is a side elevational view of the medical bandage of FIG. 1 as taken at 2—2 of FIG. 1.
Figure 3:
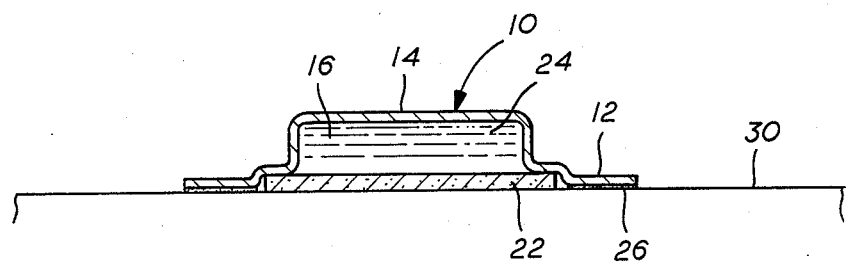
FIG. 3 is the same elevational view of the product as shown in FIG. 2 but with the protective cover removed from the face of the medical bandage and with the medical bandage applied and attached to the skin of a live subject.

The medical bandage product 10 of the present invention is illustrated in FIGS. 1–3 of the drawing with the preferred embodiment being illustrated as product 10 in FIGS. 2 and 3.

The medical bandage may be square or rectangular as shown in FIG. 1 or may be circular or of some other configuration as desired. As shown in FIG. 2, the product 10 is comprised of a liquid impermeable member 14 which forms the top and sides of a reservoir 24 which is connected in sealed relation around the edges of a permeable membrane 22 which closes the reservoir 16. The reservoir 14 may be a foil laminate of plastic and metal with the plastic being polyethylene, polyvynlchloride, or the like. The metal portion may be aluminum, for example. The permeable membrane 22 may be formed as a microporous material that will permit passage of aqueous solutions at closely controlled rates and the membrane may be formed from polymer such as polypropylene, polycarbonate, polyvynlchloride, cellulose acetate, cellulose nitrate, and the like, for example.

The permeability and the surface area of the membrane 22 is provided such that a selected amount of the aqueous fluid will pass through the membrane in a selected time period.

The impermeable membrane 14 is formed with a skirt 12 around and extending outwardly from the member 14. The face of the skirt 12 about the perimeter of the permeable member 22 is provided with a thin film of adhesive 26 such as provided on the various brands of commercial adhesive tape. The adhesive tape surface 26 and the membrane 22 is covered over by a protective shield 28 of a peal-off plastic which is also impermeable as previously described for the member 14. The reservoir 24 contains an aqueous solution 16.

The area of the permeable membrane 22 may be one square inch or greater and the volume of the reservoir 24 may contain from 2–20 cubic centimeters of the aqueous solution, for example, depending on the need such as the intended rate of administration of the aqueous solution 16 into the body and the total amount of the aqueous solution to be administered in a given period of time.

The effective constituent of the aqueous solution 16 is preferably may be either diaethelyene diamene tetracetic acid (EDTA) or trans-1,2-cyclohexane diamene tetracetic acid (CDTA). Dimethyl sulfoxide (DMSO) is the preferred constituent of the aqueous solution 16 provided as the transporting agent for the EDTA or CDTA to be transdermally transported into the body and thereon throughout the tissues of the body. While DMSO is reported to have various therapeutic qualities, its use in the present invention, as an effective constituent, is for its superior transporting characteristics.

Another constituent of the aqueous solution 16 may be a pH adjustment agent to adjust the pH of the aqueous solution to be slightly alkaline in the same range as the typical blood of a body such as a human, or a range of about pH 7.2–7.4 for example. To lower the pH, an acidic agent may be used such as acetic acid, citric acid, hydrochloric acid, or ascorbic acid, for example. To increase the pH or alkalinity, an agent such as sodium hydroxide, sodium carbonate, sodium bicarbonate, or sodium lactate, for example, may be used. The need for a pH adjustment agent will depend on the proportions of the EDTA and DMSO and perhaps other constituents used in the aqueous solution. The acids mentioned above are also considered to be chelation agents, though less effective than EDTA.

A further constituent of the aqueous solution 16 may be a vasodilator such as papavarine hydrochloride, isoxsuprine hydrochloride, cyclahdelate, and di-isopropylamine dichloroacetate, for example.

Though not essential, a gelling agent may also be used in the aqueous solution which will be filtered out as the aqueous solution is transmitted through the permeable membrane 22. Such gelling agents may be cellulose, cellulose derivities, agar tragacanth and the like. The water portion of the aqueous solution 16 is distilled water free from impurities.

As an example, the aqueous solution 16 may include constituents in the proportions of 25 parts of EDTA, 100 parts of DMSO, sodium hydroxide as necessary to give the aqueous solution a pH of 7.3 and the balance distilled water to form each cc of aqueous solution contained within the reservoir 16. The area and permeability of the permeable member 22 may be provided to allow passage of 50 milligrams of the EDTA over a 24 hour period for example. In the above example, 50 parts of papavarine hydrochloride may be incorporated for each 25 parts of EDTA as a further example.

Carter-Global Laboratories, Inc., as previously mentioned, recommends a daily dosage of disodium EDTA in amounts of 50 milligrams/kilogram of body weight to a maximum of three grams in 24 hours, which can be far greater than the above example. It is thus seen that considerable latitude in dosage is permitted within a tolerance limit of human adults.

The total dosage in a given time period in any body should be carefully designed. The dosage may be completed with the medical bandage being removed after a given time period of 3 hours to 24 hours, for example.

The advantage of the medical bandage product of the present invention and associated method is that the rate of administration may remain very small over an extended period of time to substantially reduce any adverse affects that the subject may have, and also to more carefully or exactly meter the rate by which the EDTA is administered into the subject's body. It is of course evident that there is a very large difference between the body weight of 150 pounds for a human, for example, as compared to 30 pounds for an animal being treated by a veterinarian.

When the medical bandage 10 is used, the skin on which the bandage is to be placed should be carefully washed and rinsed with water before the bandage is applied. The peel-off protector 28 is removed from the bandage 10 and the bandage 10 is firmly affixed with the skirt 12 firmly in contact with the skin and the adhesive 26 pressed down all around to the skin. The time at which the bandage 10 is applied should be noted so that the bandage may be subsequently removed after a selected amount of the EDTA has been administered. The subject should be ingesting ample water at least the rate generally recommended for good health, and more, depending on the dosage being administered.

Blind testing for the present method is simple and positive. The active product and the placebo may be identical except that the EDTA is deleted from the placebo. In use the DMSO in the placebo will cause the same characteristic garlic odor.

If the garlic odor imparted by the DMSO to a subject is at times sufficiently objectionable, the DMSO as a transporting agent may be substituted by water in the compositions herein described, so long as the pH is appropriately maintained. The resulting method and product will remain operable, though considered to be less effective.

The product 10 should be directed and prescribed by a licensed physician or veterinarian and used only under the supervision of such a physician or veterinarian.

To be noted is that the term EDTA, as used in the appended claims, is a chelation agent selected from the group consisting essentially of ethylene diamine tetracetic acid and trans 1,2-cyclohexane diamine tetracetic acid.

It will be apparent to those skilled in this art that modifications or changes may be made to the embodiment as herein described which will come within the spirit of the invention and within the purview and scope of the appended claims.

What is claimed is:

1. A chelation product comprising in combination:

(a) A membrane of selected area adapted for placement against the skin of a living body, said membrane being formed of an aqueous solution release rate controlling material that releases an aqueous solution adapted to permeate through said skin and throughout the tissues of said living body at a continuous rate over time;

(b) an aqueous liquid impermeable member connected about the edges of said membrane and having sides forming, together with said membrane, a reservoir containing said aqueous solution;

(c) said aqueous solution consisting essentially of a chelating agent, dimethylsulfoxide, a pH adjustment agent in the amount necessary to adjust the pH of said aqueous solution to a selected pH value, and water as the remainder; and (d) attachment means for retaining said membrane into contact with said skin.

2. The chelation product of claim 1, wherein said chelating agent is ethylene diamine tetracetic acid.

3. The chelation product of claim 2 wherein the pH adjustment agent is at least one of a group consisting essentially of an alkaline agent and acidic agent.

4. The chelation product of claim 1, wherein said chelating agent includes an acid selected from the group consisting essentially of acetic acid, citric acid, ascorbic acid, and hydrochloric acid.

5. The chelation product of claim 3 wherein said pH adjustment agent is at least one selected from the group consisting essentially of sodium hydrochloride, sodium bicarbonate, and sodium lactate.

6. A chelation product comprising in combination:

(a) a membrane of selected area adapted for placement in the contact against the skin of a living body, said membrane being formed of an aqueous solution release rate controlling material that releases an aqueous solution to be transported through said skin and throughout the tissues of said living body at a continuous rate over time;

(b) a reservoir formed by said membrane and an aqueous liquid impermeable member having sides connected about the edges of said membrane, said reservoir containing said aqueous solution;

(c) said aqueous solution comprising ethylene diamine tetracetic acid, a transporting agent comprising dimethylsulfoxide, a pH adjustment agent in proportion to adjust the pH of said aqueous solution, and water as the remainder; and (d) means for attaching said membrane into contact with said skin.

7. The chelation product of claim 6, wherein said chelation agent is selected from the group consisting essentially of ethylene diamine tetracetic acid and trans 1,2-cyclohexane diamine tetracetic acid.

8. The chelation product of claim 7, wherein said transporting agent is selected from the group consisting essentially of dimethylsulfoxide and water.

9. The chelation product of claim 7 wherein said pH adjustment agent is selected from the group consisting essentially of sodium bicarbonate, sodium lactate, sodium carbonate, and sodium hydroxide.

10. A chelation product comprising:

(a) a membrane of selected area adapted for placement against the skin of a living body, said membrane being formed of an aqueous solution release rate controlling material that releases an aqueous solution adapted to permeate through said skin and throughout the tissues of said body at a continuous rate over time;

(b) an aqueous liquid impermeable member connected about the edges of said membrane and having sides forming, together with said membrane, a reservoir containing said aqueous solution;

(c) said aqueous solution comprising a chelating agent selected from the group consisting essentially of ethylene diamine tetracetic acid and trans 1,2-cyclohexane diamine tetracetic acid, a transporting agent, a pH adjustment agent in an amount necessary to adjust the pH of said aqueous solution to a selected pH value, and water as the remainder; and (d) attachment means for retaining said membrane in contact with said skin.

11. The product of claim 10 wherein said chelating agent is selected from the group consisting essentially of ethylene diamine tetracetic acid, trans 1,2-cyclohexane diamine tetracetic acid, acetic acid, citric acid, ascorbic acid, and hydrochloric acid.

12. The product of claim 11 wherein said aqueous solution additionally contains a vasodilator selected from the group consisting essentially of papaverine hydrochloride isoxsuprine, hydrochloride, and cyclandelate.

13. The product of claim 10 wherein said chelation agent is selected from the group consisting essentially of ethylene diamine tetracetic acid and trans 1,2-cyclohexane diamine tetracetic acid.

14. The product of claim 11 wherein the pH adjustment agent is selected from the group consisting essentially of sodium bicarbonate, sodium lactate, sodium carbonate, and sodium hydroxide.

15. The chelation product of claim 10 wherein said chelation agent is an acid selected from the group consisting essentially of ethylene diamine tetracetic acid, trans 1,2-cyclohexane diamine tetracetic acid, acetic acid, citric acid and ascorbic acid; wherein said transporting agent is dimethylsulfoxide; and wherein said pH adjustment agent is selected from the group consisting essentially of sodium bicarbonate, sodium lactate, sodium carbonate, and sodium hydroxide.

16. A chelating product comprising:

(a) a membrane of selected area adapted for placement against a surface, said membrane being formed of an aqueous solution release rate controlling material that releases an aqueous solution at a continuous rate over time;

(b) an aqueous liquid impermeable member connected about the edges of said membrane and having sides forming, together with membrane, a reservoir containing said aqueous solution;

(c) said aqueous solution comprising a chelation agent selected from the group consisting essentially of ethylene diamine tetraacetic acid, a transporting agent selected from the group consisting essentially of dimethylsulfoxide and water, a pH adjustment agent in proportion to adjust the pH of said aqueous solution, and pH adjusting agent selected from the group, consisting essentially of sodium bicarbonate, sodium lactate, sodium carbonate, and sodium hydroxide and water as the remainder; and (d) means for attaching said membrane into contact with said surface.

* * * * *